(12) United States Patent
Dubé

(10) Patent No.: US 8,139,234 B2
(45) Date of Patent: Mar. 20, 2012

(54) METHOD AND APPARATUS FOR MEASURING OPTICAL EXTINCTION IN A THIN FILM DURING ITS DEPOSITION

(76) Inventor: George Dubé, Chesterfield, MO (US)

( * ) Notice: Subject to any disclaimer, the term of this patent is extended or adjusted under 35 U.S.C. 154(b) by 191 days.

(21) Appl. No.: 11/553,396

(22) Filed: Oct. 26, 2006

(65) Prior Publication Data

US 2010/0183800 A1  Jul. 22, 2010

Related U.S. Application Data

(60) Provisional application No. 60/729,945, filed on Oct. 26, 2005.

(51) Int. Cl.
*G01B 11/06* (2006.01)
(52) U.S. Cl. ........................................................ 356/632
(58) Field of Classification Search .................. 356/369, 356/632
See application file for complete search history.

(56) References Cited

U.S. PATENT DOCUMENTS

| 5,536,359 | A | * | 7/1996 | Kawada et al. ................. 438/16 |
| 5,548,404 | A | * | 8/1996 | Kupershmidt et al. ........ 356/368 |
| 5,838,446 | A | * | 11/1998 | Meth et al. ..................... 356/632 |
| 5,999,267 | A | | 12/1999 | Zawaideh |
| 6,091,485 | A | * | 7/2000 | Li et al. ............................ 356/73 |
| 6,285,816 | B1 | * | 9/2001 | Anderson et al. ............. 385/141 |
| 6,384,916 | B1 | * | 5/2002 | Furtak ........................... 356/369 |
| 6,392,756 | B1 | * | 5/2002 | Li et al. ......................... 356/369 |
| 6,914,675 | B1 | * | 7/2005 | Drevillon ...................... 356/369 |
| 6,917,428 | B2 | | 7/2005 | Zhu |
| 7,271,901 | B2 | * | 9/2007 | Nabatova-Gabain et al. 356/369 |

* cited by examiner

*Primary Examiner* — Tarifur Chowdhury
*Assistant Examiner* — Isiaka Akanbi
(74) *Attorney, Agent, or Firm* — Polster Lieder Woodruff & Lucchesi, L.C.

(57) ABSTRACT

A method of measuring the extinction of light in a coating including the steps of: directing a light beam to a substrate to be coated at an angle of incidence for which the beam undergoes nominal total internal reflection; depositing a coating on the substrate such that the light beam will be waveguided in the coating thus reducing internal reflection for a period of deposition time; measuring a reduction of the internal reflection during deposition; and calculating an extinction value of the light beam in the deposited layer corresponding to the measured drop in internal reflection.

16 Claims, 7 Drawing Sheets

METHOD AND APPARATUS FOR MEASURING OPTICAL EXTINCTION IN A THIN FILM DURING ITS DEPOSITION

RELATED APPLICATIONS

The present application claims priority to U.S. Provisional Patent Application Ser. No. 60/729,945 filed Oct. 26, 2005. The contents of said application are incorporated herein by reference.

STATEMENT REGARDING GOVERNMENT LICENSE RIGHTS

The U.S. Government has a paid-up license in this invention and the right in limited circumstances to require the patent owner to license others on reasonable terms as provided for by the terms of Contract FA8650-04-C-5708 awarded by the U.S. Air Force.

FIELD OF THE INVENTION

This invention relates to techniques and instruments for measuring the extinction of light by a thin film during the deposition of that coating. It is especially suited to measuring very slight extinction in a high quality optical thin film coating.

BACKGROUND OF THE INVENTION

Conventional optical component materials used to transmit high power laser beams, such as glass, fused silica, calcium fluoride and zinc selenide are heated by the laser beam. Typically the material and/or any coatings on it absorb only a very small fraction of the light, but with very high power beams even this small absorption heats the material. This heating contributes to distortion of the laser beam, whether the beam is transmitted or reflected and can stress the component beyond its elastic limit, permanently damaging it. Consequently the manufacturers of these materials endeavor to reduce the absorption of the material.

Often one or more surfaces of these components are coated with thin film optical coatings to enhance or reduce their reflection of light and/or serve other purposes such as protecting the material from chemical attack or scratches. The absorption of light by these coatings must also be minimized if the component is to be exposed to high power light beams and/or if it is important to maximize the optical efficiency of the component.

Many of these multilayer coatings use at least one thin film material that has a low (<1.5) refractive index and at least one that has a higher (>1.6) refractive index. Some coatings may contain more than 50 thin film layers. Generally, the higher refractive index (H) thin film materials absorb more light than the lower refractive index (L) thin film materials.

In order to increase the power handling capability of these coatings, the designers and manufacturers of these coatings try to reduce the absorption (extinction) of light by these coatings by purifying the materials to be coated and optimizing the coating process, which is usually performed in a vacuum chamber. Traditional ellipsometric, spectrophotometric and optical interference measurement techniques can measure the thickness and (the real part of) the refractive index of these films with adequate precision, but are seldom able to accurately measure extinction coefficients less than 10 ppm. Techniques used to measure extinction coefficients less than 10 ppm include laser calorimetry and common path interferometry. In these techniques a light beam, usually from a laser, irradiates and heats the optical component. The resulting temperature increase is measured and used to determine the absorption. The temperature increase can be measured directly (laser calorimetry) or via optical techniques (mirage technique, common path interferometry).

Currently multilayer low absorption coatings must first be deposited in a vacuum chamber, removed from the vacuum chamber and transported to a separate facility where their absorption can be measured. Often the measuring facility is in a different location than the vacuum chamber and this process can take many days. Existing techniques require a light beam powerful enough to heat the coated substrate so the temperature increase can be measured. Some techniques require, in addition, a probe light beam separate from the heating beam.

Manufacturers would like to measure the absorption of each thin film layer in real time as it is being deposited, so that process parameters can be more quickly optimized to reduce the absorption of that and subsequent layers of the same material. The process of minimizing the absorption for just one material can be lengthy as a large number of parameters are involved, including purification procedures for the raw material, preparation procedures to prepare the raw material for use in the vacuum chamber, chamber cleaning procedures, substrate cleaning and preparation procedures, substrate temperature during and immediately after deposition, chamber pressure, chamber atmosphere, deposition rate, post deposition bake-out procedures and auxiliary deposition parameters (such as ion assisted coating).

Therefore, there is a need for a method and apparatus that can measure the absorption in a low absorption thin film in real time as it is being deposited in a vacuum chamber. The results of these measurements would aid coaters in developing procedures and materials that further reduce the absorption of their coatings. This will result in lower loss coatings that will increase the power handling capability of coated optical components in high power laser applications and increase the finesse or throughput of coated optical components in sensitive instruments, such as interferometers, ringdown cavities or optical systems for microlithography and nanolithography.

SUMMARY OF THE INVENTION

The present invention provides a method of measuring the extinction of light in a coating comprising the steps of directing a light beam to a substrate to be coated at an angle of incidence for which the beam undergoes nominal total internal reflection, depositing a coating on the substrate such that an enhanced fraction of the light beam will be waveguided in the next deposited coating thus reducing internal reflection for a period of deposition time, measuring a reduction of the internal reflection during deposition, and calculating an extinction value of the light beam in the deposited layer corresponding to the measured drop in internal reflection.

DETAILED DESCRIPTION OF THE PREFERRED EMBODIMENTS

Figure 1:
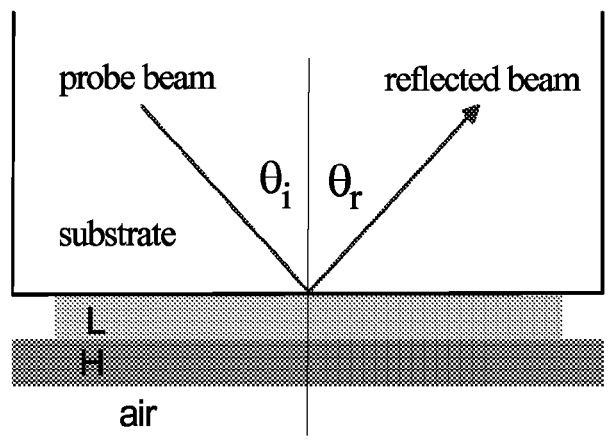
FIG. 1 is an arrangement of a probe beam for measuring the internal reflection of light.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Waveguide modes may be established in a high refractive index layer that is irradiated such that light is evanescently coupled into that high index layer. This coupling reduces the internal reflection from the total internal reflection that would occur without this coupling into the waveguide mode. This reduction can be several orders of magnitude greater than the amount of light lost to scattering and absorption in a single pass through the high index layer at normal incidence. Computer modeling showed that, for very low losses in the high index layer, the reduction in internal reflection due to waveguiding is proportional to the extinction (absorption) coefficient of the high index layer material. We therefore measure the reduction in internal reflection when the waveguide coupling is maximized and relate this measured reduction in internal reflection to the magnitude of the extinction coefficient in the high index layer via computer modeling.

FIG. 1 shows the arrangement used to measure the internal reflection of light from a coated surface. In this case, the substrate was first coated with a layer (L) that has a refractive index lower than the substrate and then with a layer (H) that has a refractive index higher than the first (L) layer. The thickness of the layers is not drawn to scale and the atmosphere next to the final layer may be air, as shown, vacuum or any atmosphere with a refractive index lower than the final coating. Typically, the thickness of each layer is less than 1000 nm. The angle of incidence ($\theta_i$) is chosen to be greater than the critical angle ($\theta_c$) for the substrate/air interface, so that the light experiences total internal reflection with or without the coatings. The angle of reflection ($\theta_r$) is equal to $\theta_i$. If an absorbing coating is applied to that surface, the total internal reflection is attenuated (reduced). If a waveguide mode is established in the high index layer its absorption reduces the total internal reflection further, often by more than one order of magnitude. A variety of techniques well known to those skilled in the art can be used to measure and record this reduction in internal reflection.

In a preferred embodiment, the angle of incidence and the wavelength of the probe beam are fixed and the internal reflectance is measured as a function of the thickness of the H* coating. In this case, the environment for the coating being deposited is generally a vacuum instead of the air environment shown in FIG. 1. Both air and vacuum have a refractive index lower than any of the solid materials. The waveguide effect again results in a drop in internal reflection over a limited range of coating thickness. With proper design, this dip will occur before the coating reaches its final thickness and the measured depth of the dip can be used to determine the extinction coefficient of the material in that thin film.

Many practical thin film coatings use multiple alternate layers that differ in refractive index, but all have an optical thickness of one quarter-wavelength. The optical thickness is the product of the refractive index (n) of the layer and the thickness of the layer (d). An optical thickness of one quarter wavelength is represented as one quarter wave optical thickness (QWOT).

Figure 2:
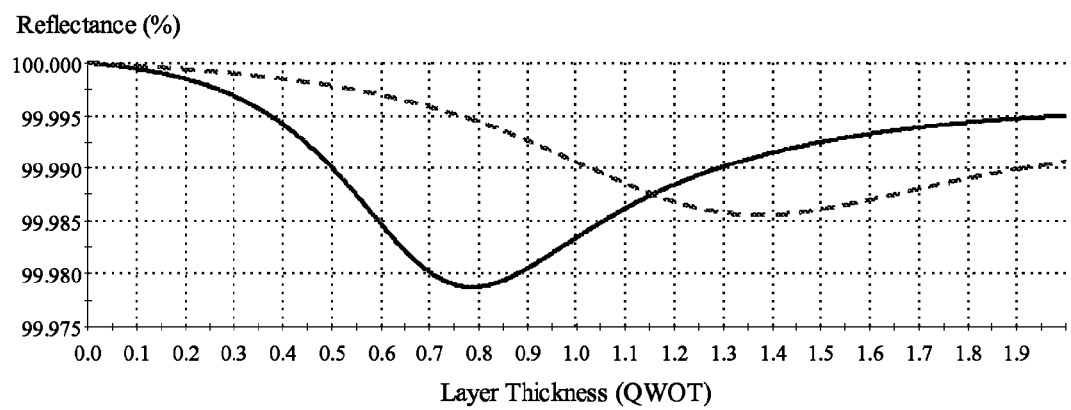
FIG. 2 shows the calculated internal reflectance at 75° angle of incidence as a 2 QWOT high index layer is deposited on a fused silica substrate with the solid line showing s-polarized light, the dotted line showing p-polarized light.

FIG. 2 shows a calculation of the internal reflectance expected from a two QWOT film H* of a high refractive index (H) material with a real part of the refractive index of 1.8352 and an absorption (extinction) coefficient (k) of 10 ppm ($1 \times 10^{-5}$) on a fused silica substrate (n=1.4600, k=1.6 ppm). The wavelength is 1315 nm and the angle of incidence is 75°

The reflection of s-polarized light dips to ~99.978 at ~0.8 QWOT and the reflection of the p-polarized light dips to ~99.985 at ~1.4 QWOT. These dips in internal reflection indicate that waveguide modes have been established in the H* layer. Computer simulations indicate that the depth of this dip (the amount of light lost from the internal reflection) is proportional to the absorption (extinction) coefficient of the H* layer. We made an instrument that measures this dip so that the absorption in the H* layer may be inferred from the depth of the dip with the help of computer modeling.

Figure 3:
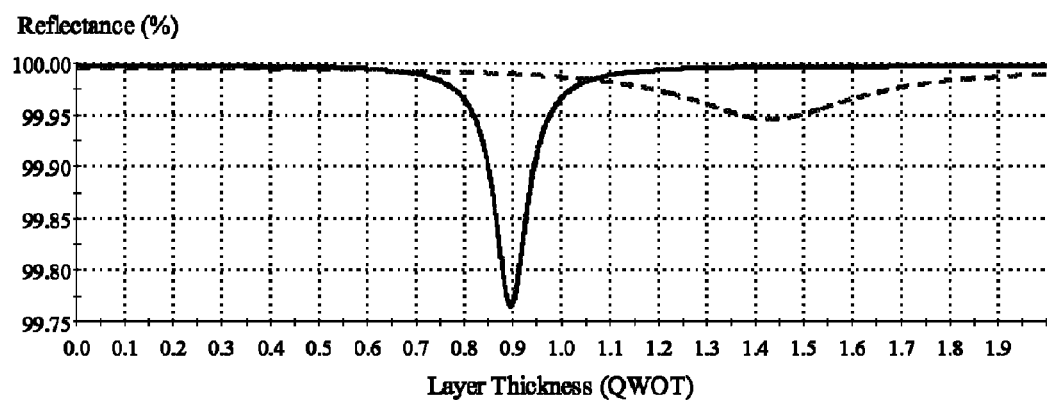
FIG. 3 shows the calculated internal reflectance at 75° angle of incidence as a 2 QWOT high index layer is deposited on a fused silica substrate/HH/LL structure with the solid line showing s-polarized light, the dotted line showing p-polarized light.

FIG. 3 shows that the calculated depth of the dip can be increased approximately tenfold by adding 2 QWOT of a high refractive index material (HH) and 2 QWOT of a low refractive index material (LL) to the fused silica substrate before the layer to be studied is deposited. H now stands for a high refractive index layer than has an optical thickness of one QWOT and L now stands for a low refractive index layer than has an optical thickness of one QWOT. The H material has n=2.1840 and k=10 ppm. The L material has n=1.4540 and k=0.

Figure 4:
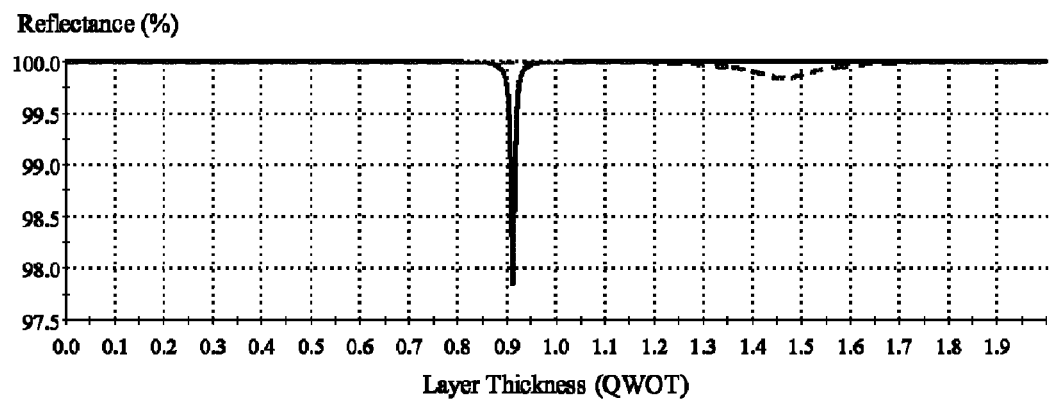
FIG. 4 shows the calculated internal reflectance at 75° angle of incidence as a 2 QWOT high index layer with extinction coefficient k=10 ppm is deposited on a fused silica/HHLLHHLL structure with the solid line showing s-polarized light, the dotted line showing p-polarized light.

FIG. 4 shows that adding an additional HH/LL coating increases the dip another tenfold to ~2.2% (100%–97.8%). We refer to each HHLL coating as one enhancement layer.

Similar calculations show that the internal reflection (dip) decreases as additional HHLL enhancement layers are added, up to four. With three enhancement layers (substrate HHLL-HHLLHHLL) the dip for s-polarized light is ~17% at 0.91 QWOT. At normal incidence a 1 QWOT of this coating will absorb approximately 0.00136%. This is the absorption that a typical laser calorimetry measurement would experience. The attenuated total internal reflection waveguide technique with three enhancement coatings increases or enhances the absorption in the hafnia layer being studied approximately 12,500 times. It is this large enhancement of the absorption that makes this technique able to measure very low extinction coefficients. A coating that absorbs 1 ppm at normal incidence will absorb 12,500 ppm or 1.25% in this technique. It is much easier to measure a drop in reflection of 1.25% than a drop of 0.0001% (1 ppm).

With four enhancement layers the dip for s-polarized light is ~85% at 0.91 QWOT, an enhancement of approximately 62,500. Adding enhancement layers become counterproductive once the dip approaches 100%. Adding a fifth HHLL enhancement layer increases the minimum reflectance to ~38% compared to the four enhancement layer reflectance of ~15%. The optimal number and type of enhancement layers varies with the extinction coefficient of the layer to be studied.

The previous simulations indicate that a few HHLL enhancement layers can significantly increase the sensitivity of this technique. Next, we demonstrate that for any particular enhancement coating, the depth of the dip (decrease) in internal reflection is proportional to the extinction coefficient of the material being deposited and studied.

Figure 5:
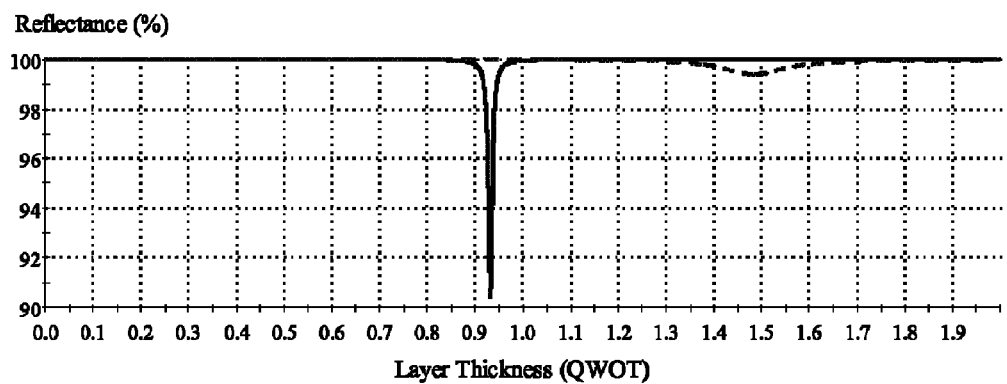
FIG. 5 shows the calculated internal reflectance at 75° angle of incidence as a 2 QWOT high index layer with extinction coefficient k=50 ppm is deposited on a fused silica/HHLLHHLL structure with the solid line showing s-polarized light, the dotted line showing p-polarized light.
Figure 6:
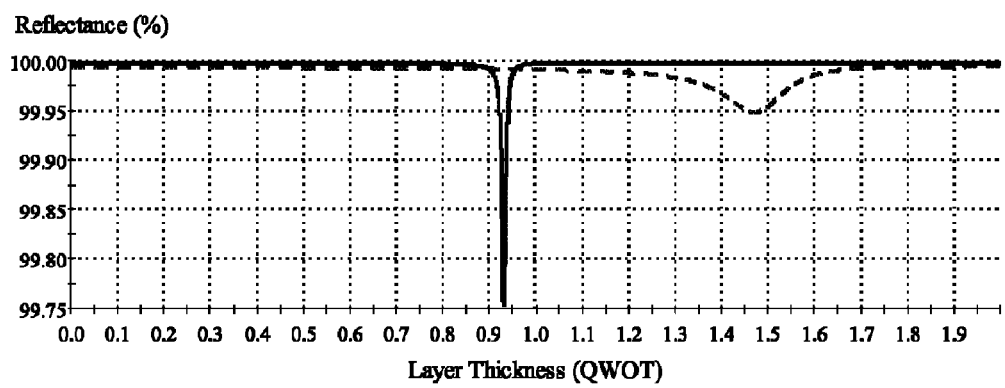
FIG. 6 shows the calculated internal reflectance at 75° angle of incidence as a 2 QWOT lossless (k=0) high index layer is deposited on a fused silica/HHLLHHLL structure with the solid line showing s-polarized light, the dotted line showing p-polarized light.

FIG. 5 shows the same enhancement layer shown in FIG. 4, but the extinction coefficient of the H* (hafnia) layer being studied has increased from 10 ppm to 50 ppm. A five fold increase in the extinction coefficient has resulted in a 4.4-fold increase in the depth of the dip for the s-polarized light (from 2.2% to 9.7%). In both FIGS. 4 and 5, ~0.25% of the dip for s-polarized light is due to the absorption of light in the HHLL-HHLL enhancement coatings (see FIG. 6).

The increase in dip (decrease in internal reflection) is very nearly proportional to the extinction coefficient in the H* layer being studied. Strict proportionality is not required as the results may readily be computer modeled.

One of the simplest enhancement layers is a single low index layer of thickness greater than 4 QWOT. However, it is often difficult for coaters to produce high quality low refractive index films that thick. Other enhancement coating designs also work well, as indicated by the following examples.

Figure 7:
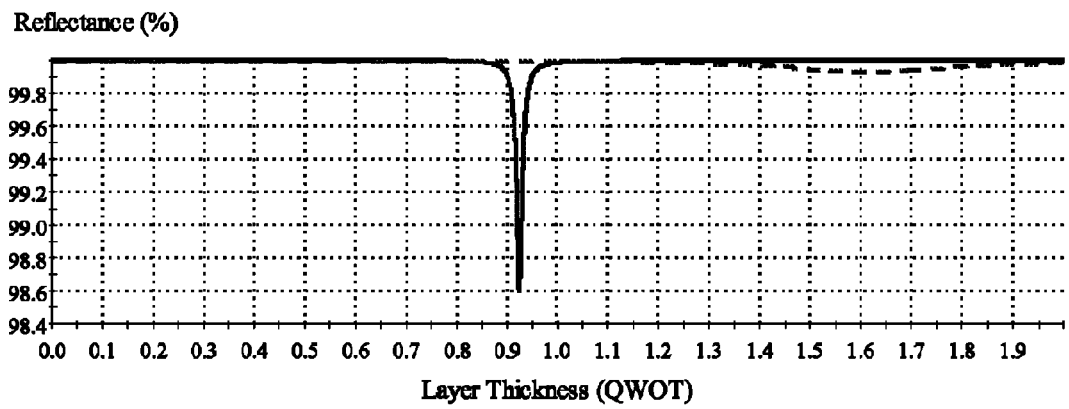
FIG. 7 shows the calculated internal reflectance at 70° angle of incidence as a 2 QWOT high index layer with extinction coefficient k=10 ppm is deposited on a fused silica/1.6HLL1.6HLL structure with the solid line showing s-polarized light, the dotted line showing p-polarized light.

FIG. 7 shows the same case as FIG. 4, but the thickness of each of the four layers in the HHLLHHLL enhancement coating has been reduced from 2 QWOT to 1.6 QWOT. The dip is reduced from 2.2% to 1.4%, but remains useful. The angle of incidence was changed to 70° to keep the dip at a layer thickness just less 1 QWOT.

Figure 8:
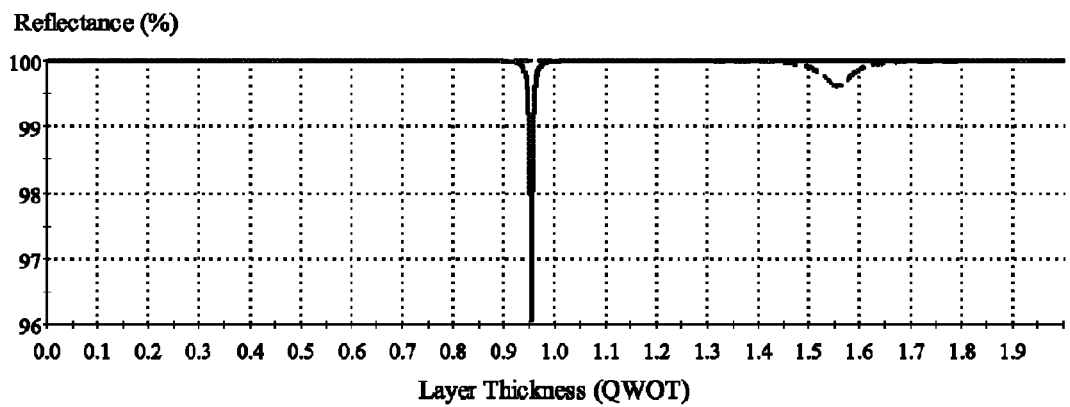
FIG. 8 shows calculated internal reflectance at 80° angle of incidence as a 2 QWOT high index layer is deposited on a fused silica/1.6H1.6L2.4H2.4L structure with the solid line showing s-polarized light, the dotted line showing p-polarized light.

FIG. 8 shows the case where the first H and L coatings are 1.6 QWOT and the second H and L coatings are 2.4 QWOT.

Figure 9:
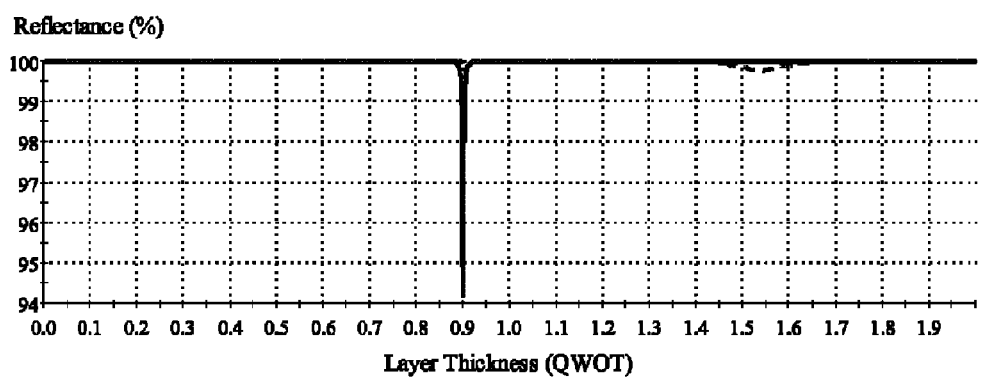
FIG. 9 shows calculated internal reflectance at 75° angle of incidence as a 2 QWOT high index layer is deposited on a fused silica/1.6H2.4L1.6H2.4L structure with the solid line showing s-polarized light, the dotted line showing p-polarized light.

In FIG. 9 both high index layers are 1.6 QWOT and both low index layers are 2.4 QWOT. Computer simulations indicate that the absorption in a single high index thin film (H*) can be increased many thousands of times by using enhancement coatings with this attenuated total internal reflection-waveguide technique and that over a wide range of parameters the depth of the dip in internal reflection is proportional to and can be used to determine the extinction coefficient of that H* film.

For the dip to be useful it must occur before the layer being deposited reaches its final thickness. For some applications it is desirable to have the dip in internal reflection occur at a layer thickness slightly less than 1.0 QWOT. If the dip occurs at a much thinner layer there may be doubt that the rest of the material deposited after the dip has the same properties as the material deposited before the dip.

The layer thickness at which the dip occurs can be increased by the following adjustments:
1. Optically thinner enhancement layers
2. Greater angle of incidence
3. Higher substrate refractive index
4. Lower refractive index of the layer being studied With the proper choice of the parameters listed above a suitable enhancement layer and configuration can be created for any high index layer of any practical thickness.

Figure 10:
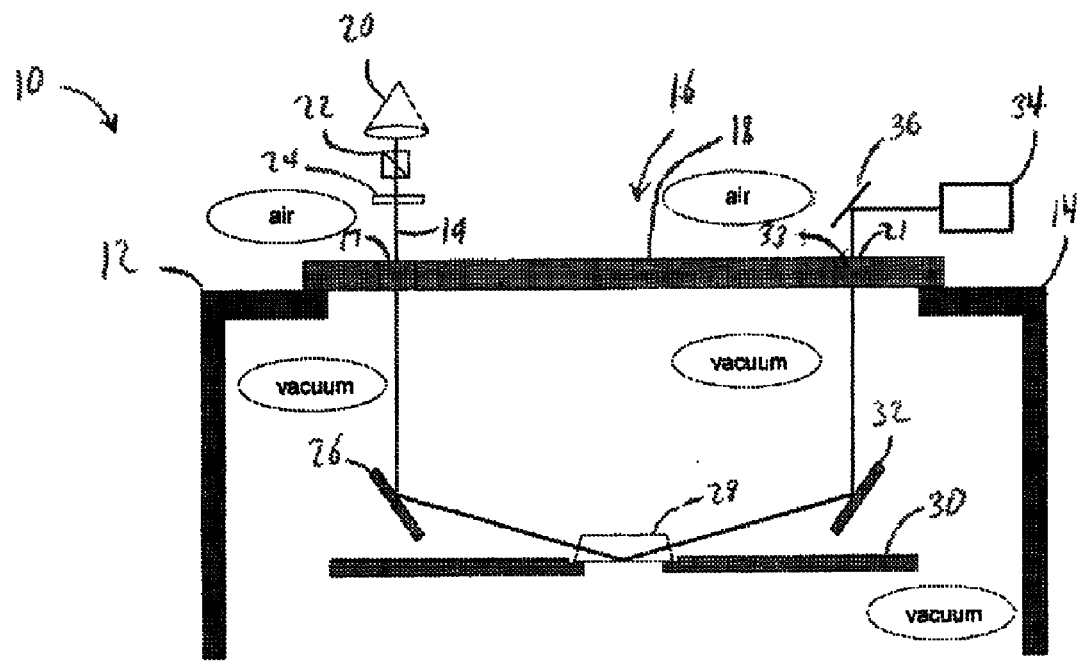
FIG. 10 is a diagram of a preferred embodiment for measuring the extinction in a thin film during its deposition according to an embodiment of the present invention.

FIG. 10 is a diagram of the instrument constructed and used to measure the absorption in a thin film during its deposition. Only an upper portion 12 of a vacuum chamber 10 is shown. The vacuum chamber comprises a vacuum chamber wall 14 having an opening 16 covered by a top plate 18 containing vacuum-tight windows 17 and 33. A vacuum is created inside the vacuum chamber 10 by a vacuum pump (not shown). A beam of light 19 is directed through a fiber to laser collimator 20 through a polarizer 22 and a rotating halfwave plate 24 and window 17 into the vacuum chamber. Inside the vacuum chamber the beam of light 19 contacts a mirror 26 and is directed to a custom substrate 28 being examined where it experiences total internal reflection from the surface to be coated 29. The custom substrate is supported by a sample support plate 30. Another mirror 32 directs the beam of light 19 reflected from the custom substrate 28 through a second vacuum tight window 33 out of the vacuum chamber to a detector 34 or other mirrors 36 which direct the beam of light 19 to the detector 34.

The material for coating the substrate 28 is located in the lower portion (not shown) of the vacuum chamber 10. A 1315 nm probe beam is generated by a laser diode (not shown) to generate the beam of light.

The probe light 19 reaching the surface to be coated 29 is always linearly polarized, but its axis of polarization is rotating at four times the rotation rate of the half wave plate 24.

In practice, there would typically be one or more substrates near the custom substrate that would receive the same deposition as the custom substrate 28. In some cases, the substrates are rotated or moved during the deposition to ensure that all substrates receive coatings of the same thickness.

Figure 11:
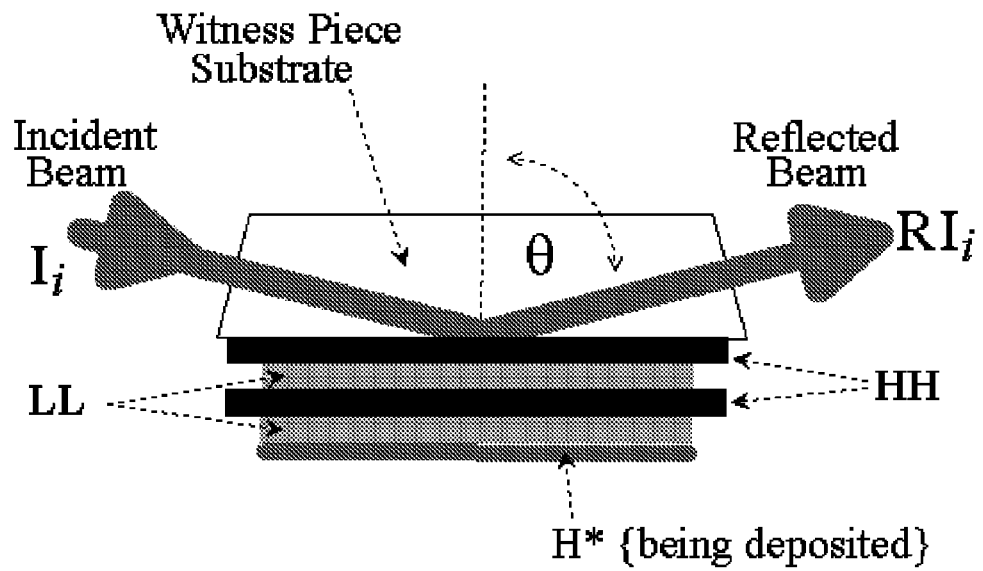
FIG. 11 is a more detailed diagram of the witness piece with a two layer enhancement coating according to an embodiment of the present invention.

All four surfaces of the substrate shown in FIGS. 10 and 11 are optically polished. The lower surface 29 was superpolished to a very smooth finish. The other three surfaces received a more ordinary optical polish. The substrate material was Infrasil 302 fused silica. This particular test substrate was designed for an angle of incidence of 75°. The two side faces are 15° from the vertical direction so the probe beam will be normal to each face when it is reflected from the bottom surface at an angle of incidence of 75°.

Figure 12:
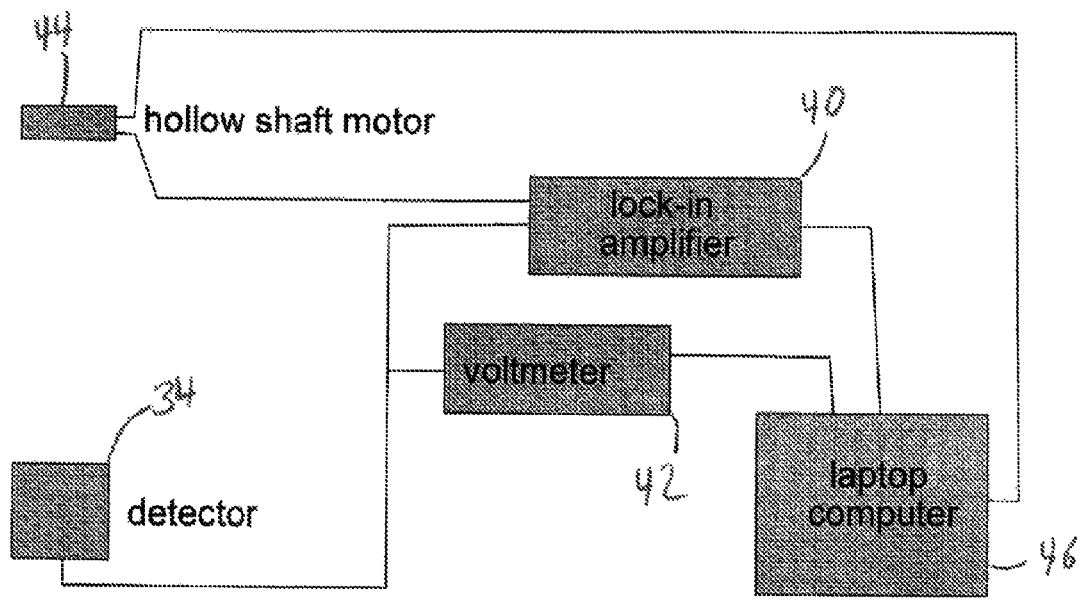
FIG. 12 is an electrical diagram of the instrument used to measure absorption in a thin film during its deposition according to an embodiment of the present invention.

Referring to FIG. 12, an output signal from the detector 34 was routed to a phase sensitive lock in an amplifier 40 and a recording voltmeter 42. An encoder signal from a hollow shaft motor 44 that rotates the half wave plate 24 is sent to the lock-in amplifier 40 to establish a lock-in frequency. The lock-in amplifier 40 was then tuned to the fourth harmonic of this frequency.

Figure 13:
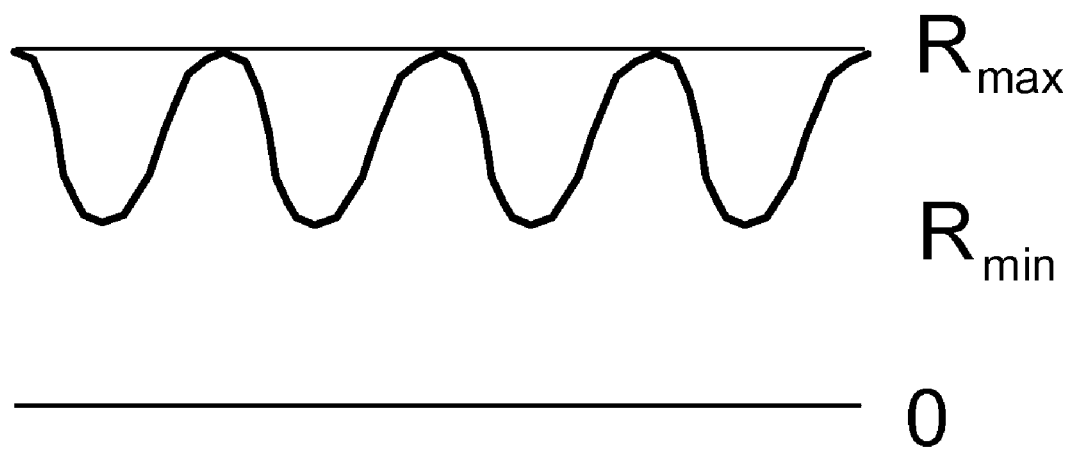
FIG. 13 is a diagram of an oscillating voltage output signal from a photo detector according to an embodiment of the present invention.

The output signal from the photodetector is sketched in FIG. 13. The maximum signal ($R_{max}$) is proportional to the highest reflectivity (usually 100%, total internal reflection) from the surface being probed and coated. The minimum signal ($R_{min}$) is proportional to the lowest reflectivity at the depth of the dip in internal reflection. If a rotating halfwave plate is employed, the frequency of this oscillation is four times the frequency of the rotation of the halfwave plate.

When light of both polarizations is 100% reflected at the probed surface, there is no AC signal at the fourth harmonic. The detector 34 output is constant and the output signal from the lock-in amplifier 40 is zero. If only one polarization dips below 100%, the lock-in amplifier output is proportional to that dip ($R_{max}$–$R_{min}$). The greatest detector 34 output establishes the 100% reflection signal and is used to normalize the reduced signal.

In practice, there is typically a lock-in signal before the coating starts as the probe beam 19 passes through numerous surfaces at other than normal incidence. At other than normal incidence, the transmission of s-polarized light is slightly less than the transmission of p-polarized light, so the lock-in amplifier 40 has an output. This output remains unchanged before, during and after the deposition of the coating to be studied. This baseline output must be subtracted from the recorded signal to obtain the desired signal due to the waveguide mode in the H* film.

The amplitude and phase of the lock-in amplifier 40 output and the signal from the detector are recorded with the computer 46 as the coating is deposited. If the lock-in amplifier 40 displays the rms value of the synchronous signal, that value must be multiplied by 2.828 to convert it to a peak-to-valley value. That value must then be normalized by dividing it by the peak photodetector output signal (for the polarization that does not drop) at the time of the drop in internal reflection for the other polarization.

The above example shows that the invention, as defined by the claims, has far ranging application and should not be limited merely to the embodiment shown and described in detail. Instead the invention should be limited only to the explicit words of the claims, and the claims should not be limited to embodiment shown in the specification merely because a single example may be shown. The scope of protection is only limited by the scope of the accompanying claims, and the Examiner should examine the claims on that basis.

What is claimed is:

1. A method of measuring the extinction of light in a coating as it is being deposited, comprising the steps of:
    depositing at least one pair of thin film layers comprising a first layer and a second layer with refractive index at least 0.10 lower than the refractive index of the first layer, each layer within any pair having optical thickness between about 1.4 and 2.5 quarter wavelengths, and
    sending at least one nominally collimated probe light beam from a substrate side of a substrate surface to be coated such that the beam encounters that surface at an angle of incidence for which the beam undergoes nominal total internal reflection prior to the deposition of the coating to be studied and such that the probe beam will, at a certain layer thickness less than the intended final thickness, be waveguided in that layer thus reducing the internal reflection for some limited period of deposition, and
    measuring any reduction(s) of the internal reflection during the deposition and calculating the extinction(s) in that deposited waveguiding layer that correspond(s) to the measured drop(s) in internal reflection.

2. The method of claim 1 in which at least the measured portion of the probe beam is nominally monochromatic.

3. The method of claim 1 in which the internal reflection is measured for s and/or p linearly polarized light with respect to the surface being coated.

4. The method of claim 3 in which the linear polarization of the probe light beam is regularly changed from "s" to "p" polarization with respect to the surface being probed.

5. The method of claim 4 in which the half wave plate is rotated by being mounted in a rotating hollow shaft motor.

6. The method of claim 4 in which phase sensitive lock-in amplifier is used to synchronously measure the polarization dependent change of the internal reflection of the probe beam.

7. The method of claim 6 in which the output from the lock-in amplifier and a signal from a detector are measured.

8. The method of claim 3 in which the linearly polarized probe light beam is passed through a rotating half wave plate to continuously change the probe light between s and p polarization at the surface to be probed.

9. A method of measuring the extinction of light in a coating comprising the steps of:
    directing a light beam to a substrate to be coated at an angle of incidence for which the beam undergoes nominal total internal reflection;
    depositing an enhancement coating on the substrate such that the light beam will be waveguided in the next coating deposited thus reducing internal reflection for a period of deposition time;
    measuring a reduction of the internal reflection during deposition;
    calculating an extinction value of the light beam in the deposited layer corresponding to the measured drop in internal reflection, and
    wherein the enhancement coating comprises at least one pair of layers comprising of a first layer and a second layer with refractive index at least 0.10 lower than the refractive index of the first layer, each layer within any pair having an optical thickness between about 1.4 and about 2.5 quarter wavelengths.

10. The method of claim 9 further comprising the step of nominally linearly polarizing the light beam.

11. The method of claim 10 further comprising the step of alternatingly changing the polarization of the light beam from s- to p-polarization with respect to the substrate.

12. The method of claim 11 further comprising the step of using an electro-optic device to change the polarization of the light.

13. The method of claim 11 further comprising the step of passing the light beam through a rotating half wave plate to alternatingly change the probe light between s- and p-polarization.

14. The method of claim 13 wherein the half wave plate mounted in a rotating hollow shaft motor.

15. The method of claim 9 in which the light beam is sent to and the coating is applied to a test piece or surface area separate from the substrate that does not have a coating and will receive the same deposition.

16. A method of measuring the extinction of light in a coating during its deposition comprising the steps of:
    depositing an enhancement coating on a substrate such that an increased fraction of a probe light beam will be coupled into a waveguide in a next layer to be deposited before that layer reaches its final thickness thus reducing internal reflection of a probe beam for a period of deposition time;

directing a nominally collimated probe light beam to this enhancement coated substrate at an angle of incidence for which the beam undergoes nominal total internal reflection;

measuring a reduction of the internal reflection during deposition;

calculating an extinction value of the light beam in the deposited layer corresponding to the measured drop in internal reflection; and wherein the enhancement coating comprises at least one pair of layers comprising of a first layer and a second layer with refractive index at least 0.10 lower than the refractive index of the first layer, each layer within any pair having an optical thickness between about 1.4 and about 2.5 quarter wavelengths.

* * * * *